(12) United States Patent
Kim

(10) Patent No.: US 11,730,425 B2
(45) Date of Patent: Aug. 22, 2023

(54) SIGNAL MEASUREMENT APPARATUS AND SIGNAL MEASUREMENT METHOD

(71) Applicant: Samsung Electronics Co., Ltd., Suwon-si (KR)

(72) Inventor: Jongpal Kim, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 807 days.

(21) Appl. No.: 16/734,759

(22) Filed: Jan. 6, 2020

(65) Prior Publication Data

US 2021/0085250 A1  Mar. 25, 2021

(30) Foreign Application Priority Data

Sep. 20, 2019  (KR) .................. 10-2019-0116100

(51) Int. Cl.
*A61B 5/00* (2006.01)
*A61B 5/0535* (2021.01)
*H03F 3/45* (2006.01)
*A61B 5/304* (2021.01)

(52) U.S. Cl.
CPC .......... *A61B 5/6825* (2013.01); *A61B 5/0535* (2013.01); *A61B 5/304* (2021.01); *H03F 3/45* (2013.01)

(58) Field of Classification Search
CPC ..... A61B 5/6825; A61B 5/0535; A61B 5/304; H03F 3/45
See application file for complete search history.

(56) References Cited

U.S. PATENT DOCUMENTS

| 9,545,212 | B2 | 1/2017 | Kim |
| 9,615,744 | B2 | 4/2017 | Denison et al. |
| 9,729,109 | B2 | 8/2017 | Shu et al. |
| 9,888,863 | B2 | 2/2018 | Biancolillo et al. |
| 9,912,309 | B1 | 3/2018 | Ecker et al. |
| 10,141,918 | B2 | 11/2018 | Kim |
| 2017/0126216 | A1* | 5/2017 | Kim .................. A61B 5/30 |
| 2018/0287567 | A1* | 10/2018 | Sugiura .................. H03F 3/45 |

FOREIGN PATENT DOCUMENTS

| JP | 3062506 B1 | 7/2000 |
| JP | 5233882 B2 | 7/2013 |
| JP | 2018-522637 A | 8/2018 |
| KR | 10-2015-0025109 A | 3/2015 |
| KR | 10-2019-0064987 A | 6/2019 |

* cited by examiner

*Primary Examiner* — Joseph M Dietrich
(74) *Attorney, Agent, or Firm* — NSIP Law

(57) ABSTRACT

A signal measurement apparatus and signal measurement method are provided. The signal measurement apparatus includes an amplifier configured to receive a differential voltage signal, amplify the received differential voltage signal, and output the amplified differential voltage signal, a controller configured to output a control signal to control a switching circuit in response to a signal value of the amplified differential voltage signal satisfying a condition, and wherein the switching circuit is configured to change connections between input terminals of the amplifier and paths along which the differential voltage signal is transmitted, based on the control signal.

18 Claims, 7 Drawing Sheets

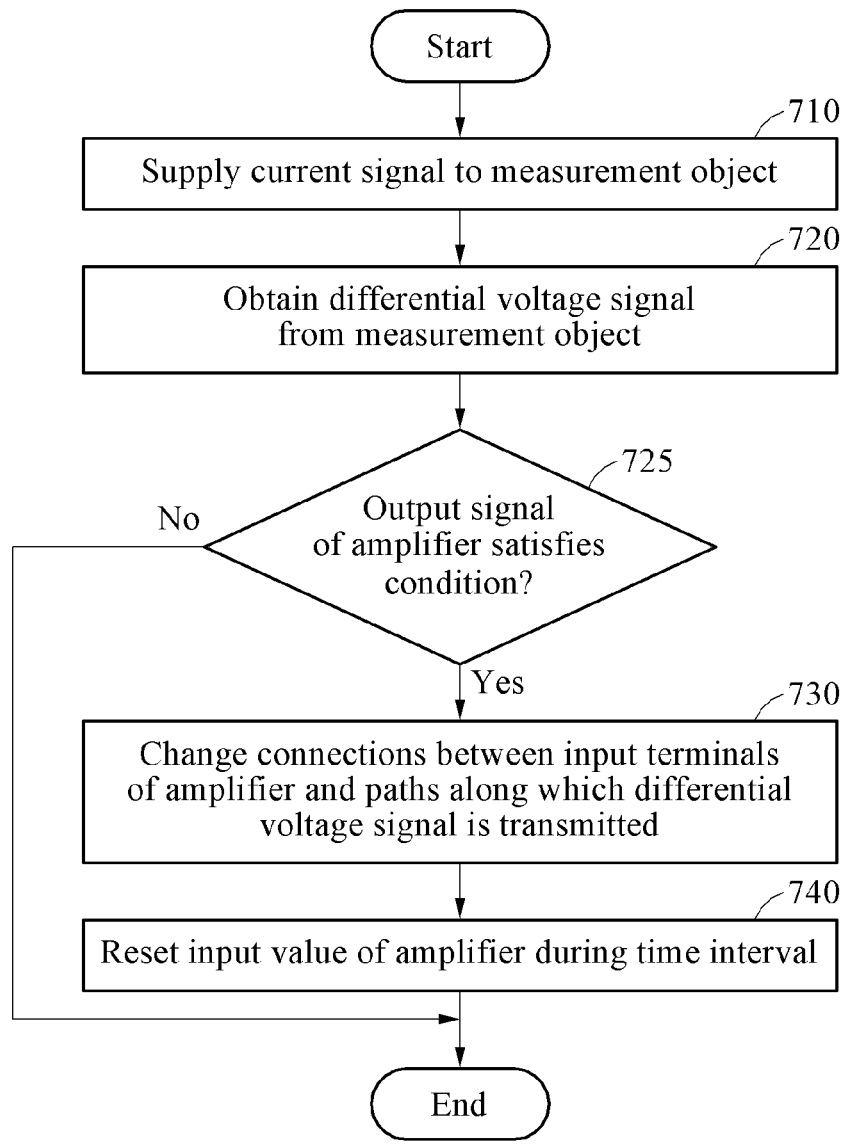

SIGNAL MEASUREMENT APPARATUS AND SIGNAL MEASUREMENT METHOD

CROSS-REFERENCE TO RELATED APPLICATIONS

This application claims the benefit under 35 USC § 119(a) of Korean Patent Application No. 10-2019-0116100 filed on Sep. 20, 2019 in the Korean Intellectual Property Office, the entire disclosure of which is incorporated herein by reference for all purposes.

BACKGROUND

Field

The following description relates to signal measurement technology, and specifically, a signal measurement apparatus and a signal measurement method.

Description of Related Art

A body, for example, a human body, includes biological tissues having various electrical characteristics. The biological tissues have a conductivity through ions that may carry electric charges. Biological tissues of different parts of the body may have different levels of conductivity. Biological tissues of muscles have a characteristic of a conductor that allows a flow of current, whereas biological tissues of bones have a characteristic of a nonconductor that does not allow a flow of current. The biological tissues have electrical resistance characteristics or reactance characteristics. A portion of the biological tissues may transmit a high-frequency input signal in an ohm manner, and another portion of the biological tissues may transmit a low-frequency input signal in a capacitor manner. To measure the impedance of biological tissues, a small alternating current is applied to the biological tissues, and an alternating voltage induced by the corresponding alternating current is measured. The magnitude of the alternating current applied to the biological tissues is known information, and thus the bioimpedance may be estimated by analyzing the measured alternating voltage based on Ohm's law.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In a general aspect, a signal measurement apparatus includes an amplifier configured to receive a differential voltage signal, amplify the received differential voltage signal, and output the amplified differential voltage signal; and a controller configured to output a control signal to control a switching circuit in response to a signal value of the amplified differential voltage signal satisfying a condition; wherein the switching circuit is configured to change connections between input terminals of the amplifier and paths along which the differential voltage signal is transmitted, based on the control signal.

The switching circuit may be further configured to reverse the connections based on the control signal.

The controller may be further configured to output a control signal to change a connection of the switching circuit, in response to the signal value of the amplified differential voltage signal reaching a first threshold value.

The controller may be further configured to output the control signal to change the connection of the switching circuit, in response to the signal value of the output signal of the amplifier reaching the first threshold value and then reaching a second threshold value, wherein the first threshold value and the second threshold value are different values.

The controller may include a counter configured to count a number of times the signal value of the amplified differential voltage signal reaches a threshold value.

The controller may be further configured to reset a count value output from the counter in a time interval after the signal value of the amplified differential voltage signal is sampled.

An actual signal value of the amplified differential voltage signal may be estimated based on the signal value of the amplified differential voltage signal at a time corresponding to a 90-degree phase of a current source, a determined count value of the counter, and the threshold value.

The controller may be further configured to output a control signal to input a reset signal into the input terminals of the amplifier during a time interval after the signal value of the amplified differential voltage signal is sampled.

In response to the reset signal being input to the input terminals of the amplifier, the amplified differential voltage signal may indicate a constant value.

The time interval may be a time interval from a time corresponding to a 180-degree phase of the current source to a time corresponding to a 360-degree phase of the current source.

The switching circuit may include a chopper circuit configured to control connections between the input terminals of the amplifier and paths along which first and second voltage signals included in the differential voltage signal are supplied.

In a general aspect, a signal measurement method includes transmitting, by a signal measurement apparatus, a current signal to a measurement object; receiving, by the signal measurement apparatus, a differential voltage signal induced by the current signal from the measurement object; inputting the received differential voltage signal to an amplifier; and changing connections between input terminals of the amplifier and paths along which the differential voltage signal is transmitted, in response to a signal value of an output signal of the amplifier satisfying a condition.

The changing of the connections may include changing the connections with a switching circuit positioned between the paths along which the differential voltage signal is transmitted and the amplifier.

The changing of the connections may include changing the connections in response to the signal value of the output signal of the amplifier reaching a first threshold value.

The changing of the connections may further include changing the connections to an original state in response to the signal value of the output signal of the amplifier reaching the first threshold value and then reaching a second threshold value.

The signal measurement apparatus may be configured to count a number of times the signal value of the output signal of the amplifier reaches a threshold value, and estimate an actual signal value of the output signal of the amplifier based on a signal value of the output signal of the amplifier at a time corresponding to a 90-degree phase of a current source, a determined count value, and the threshold value.

The method may further include resetting an input value of the amplifier during a time interval after the signal value of the output signal of the amplifier is sampled.

In a general aspect, a signal measurement apparatus includes a receiver configured to receive a measured differential voltage signal; a capacitor configured to remove a voltage component from the differential voltage signal and output a resultant differential voltage signal; a switching circuit configured to receive the resultant differential voltage signal and adjust a polarity of the resultant differential voltage signal; and an amplifier configured to receive the adjusted resultant differential voltage signal, amplify the adjusted resultant differential voltage signal, and output the amplified signal.

The switching circuit may include a chopper circuit configured to control connections between input terminals of the amplifier and paths along which first and second voltage signals included in the received differential voltage signal are supplied.

Other features and aspects will be apparent from the following detailed description, the drawings, and the claims.

BRIEF DESCRIPTION OF DRAWINGS

FIG. 7 illustrates an example of a signal measurement method, in accordance with one or more embodiments.

Figure 1:
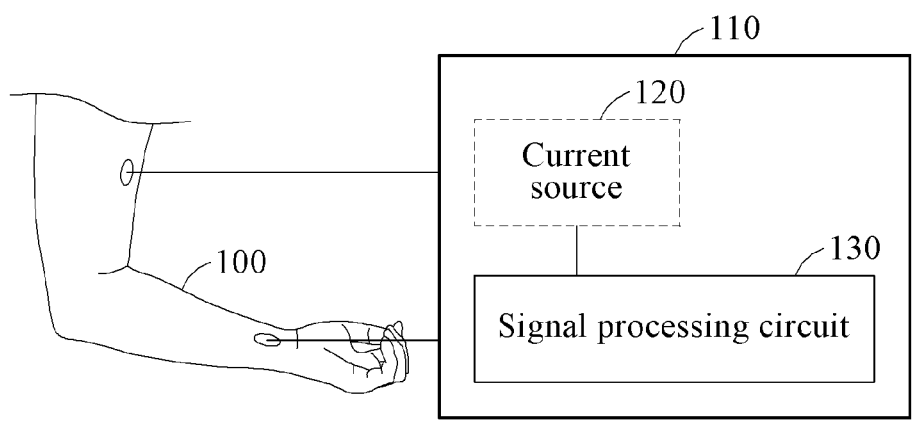
FIG. 1 illustrates an example of an overview of a signal measurement apparatus, in accordance with one or more embodiments.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known in the art may be omitted for increased clarity and conciseness.

The features described herein may be embodied in different forms and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

The following structural or functional descriptions of examples disclosed in the present disclosure are merely intended for the purpose of describing the examples and the examples may be implemented in various forms. The examples are not meant to be limited, but it is intended that various modifications, equivalents, and alternatives are also covered within the scope of the claims.

Although terms of "first" or "second" are used to explain various components, the components are not limited to the terms. Each of these terminologies is not used to define an essence, order or sequence of a corresponding component but used merely to distinguish the corresponding component from other component(s). For example, a "first" component may be referred to as a "second" component, or similarly, and the "second" component may be referred to as the "first" component within the scope of the right according to the concept of the present disclosure. In addition, it should be noted that if it is described that one component is "connected", "coupled", or "joined" to another component, a third component may be "connected", "coupled", and "joined" between the first and second components, although the first component may be directly connected, coupled, or joined to the second component.

The singular forms "a", "an", and "the" are intended to include the plural forms as well, unless the context clearly indicates otherwise. It will be further understood that the terms "comprises/comprising" and/or "includes/including" when used herein, specify the presence of stated features, integers, steps, operations, elements, and/or components, but do not preclude the presence or addition of one or more other features, integers, steps, operations, elements, components and/or groups thereof.

Unless otherwise defined herein, all terms used herein including technical or scientific terms have the same meanings as those generally understood. Terms, such as those defined in commonly used dictionaries, are to be interpreted as having a meaning that is consistent with their meaning in the context of the relevant art and the present disclosure, and are not to be interpreted in an idealized or overly formal sense unless expressly so defined herein.

Hereinafter, examples will be described in detail with reference to the accompanying drawings. Like reference numerals in the drawings denote like elements, and thus their description will be omitted.

FIG. 1 illustrates an example of an overview of a signal measurement apparatus, in accordance with one or more embodiments.

Referring to FIG. 1, a signal measurement apparatus 110 may be an apparatus for measuring a signal, which, for example, measures an impedance signal of a measurement object 100. The measurement object 100 is a living body. A signal measured from a living body is referred to as a biosignal, and the biosignal includes a bioelectric signal and a bioimpedance signal. The biosignal changes depending on a biological activity, for example, breathing, or a biological state. A state of the measurement object 100 is estimated based on a result of analyzing such a change in the biosignal. For example, the signal measurement apparatus 110 measures a biosignal from the measurement object 100, and processes the measured biosignal to be in a form that is easy to analyze.

The signal measurement apparatus 110 may include a current source 120 configured to supply a current signal, for example, an alternating current signal, to the measurement object 100, and a signal processing circuit 130 configured to measure a voltage signal, for example, an alternating voltage signal, received from the measurement object 100 and process the measured voltage signal. In an example, the current source 120 may be provided separately from the signal measurement apparatus 110, rather than being included in the signal measurement apparatus 110. A magnitude, a frequency, and a signal waveform of the current signal supplied from the current source 120 may be known. The current signal output from the current source 120 may be transmitted to the measurement object 100 through an electrode pair attached to the measurement object 100 in a contact or non-contact manner. The signal measurement apparatus 110 may sense the voltage signal induced by the current signal from the measurement object 100 through another electrode pair attached to the measurement object 100. The use of the term "may" herein with respect to an example or embodiment, e.g., as to what an example or embodiment may include or implement, means that at least one example or embodiment exists where such a feature is included or implemented while all examples and embodiments are not limited thereto.

The signal processing circuit 130 may be a circuit configured to process the sensed voltage signal. The signal processing circuit 130 may include an amplifier configured to amplify the voltage signal measured from the measurement object 100, a controller configured to control an operation of the signal processing circuit 130, and a converter configured to sample a signal value of the voltage signal amplified by the amplifier and convert an analog signal to a digital signal based on the sampled signal value.

A predetermined current signal is applied to the measurement object 100 through the current source 120, and an impedance of the measurement object 100 is estimated by measuring a voltage signal induced by the current signal applied to the measurement object 100. For example, if a predetermined current signal I supplied to the measurement object 100 is known and a voltage signal V measured from the measurement object 100 is known, an impedance Z of the measurement object 100 is estimated according to the Ohm's law (Z=V/I).

An impedance component included in the voltage signal measured from the measurement object 100 includes a static impedance component and a dynamic impedance component. The dynamic impedance component is an impedance component which corresponds to a change in a signal responding to breathing or stimulation and is an object of interest. Conversely, the static impedance component is an impedance component irrelevant to breathing or stimulation and is not an object of interest. If a static impedance component including a direct current impedance component is great, the proportion of the static impedance component in the measured voltage signal is also great. The range of an impedance component to be measured is in the form having an alternating current impedance component Rac with a minute change range based on a relatively great direct current impedance component Rdc, rather than the form with the range from "0" to a maximum impedance value Rmax.

Before estimating the impedance Z of the measurement object 100, the signal measurement apparatus 110 amplifies the measured voltage signal through the amplifier included in the signal processing circuit 130. In a process of amplifying the measured signal, if the amplified signal is out of the range of the signal that may be handled by the signal processing circuit 130, saturation may occur, where the amplified signal does not follow the change pattern of the originally measured signal, and may be fixed to a predetermined signal value. If saturation occurs, meaningful information included in the measured signal may not be used. Thus, saturation is not desirable. If the range of the signal that may be handled by the signal processing circuit 130 is designed to be wide to lower the probability of the occurrence of saturation, relatively high-performance elements may be desired, which decreases the efficiency.

Meanwhile, an operating voltage of a measurement circuit for signal measurement may decrease. In response to the decrease, the signal range for measuring an analog signal is gradually limited. If the signal range that may be measured by the measurement circuit is narrow, a signal beyond the signal range may not be measured in a normal manner.

According to examples set forth hereinafter, the signal measurement apparatus 110 and a signal measurement method performed by the signal measurement apparatus 110 that may overcome the issues described above are provided. The signal measurement apparatus 110 provides a solution to overcome the issues described above, by changing connections between input terminals of an amplifier and path along which the measured signal is transmitted at a time at which the measured voltage signal reaches a predetermined threshold value, which will be described further below.

Figure 2:
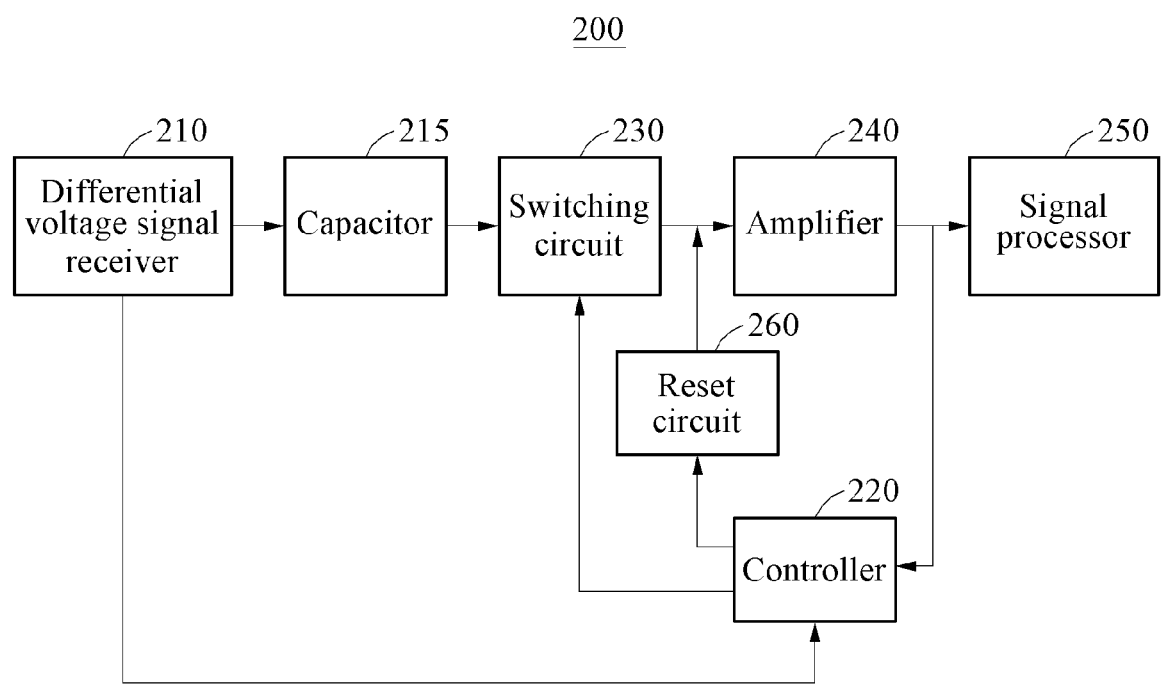
FIG. 2 illustrates an example of a configuration of a signal measurement apparatus, in accordance with one or more embodiments.

FIG. 2 illustrates an example of a configuration of a signal measurement apparatus in accordance with one or more embodiments.

Referring to FIG. 2, a signal measurement apparatus 200 includes a differential voltage signal receiver 210, a capacitor 215, a controller 220, a switching circuit 230, an amplifier 240, a signal processor 250, and a reset circuit 260.

The differential voltage signal receiver 210 obtains a measured differential voltage signal. The differential voltage signal receiver 210 includes a current source (not shown) configured to transmit a predefined current signal to a measurement object, and obtain a differential voltage signal induced by the current signal from the measurement object. The differential voltage signal includes a first voltage signal of a first polarity, for example, a positive pole, and a second voltage signal of a second polarity, for example, a negative pole, different from the first polarity.

The voltage signal obtained by the differential voltage signal receiver 210 is transmitted to the capacitor 215. The capacitor 215 removes a direct voltage component from the obtained differential voltage signal and outputs the resultant differential voltage signal. The differential voltage signal measured from the measurement object is transmitted to one end of the capacitor 215, and the other end of the capacitor 215 is connected to the switching circuit 230.

The amplifier 240 amplifies and outputs the voltage signal input through an input terminal of the amplifier 240. In an example, the amplifier 240 may be a differential amplifier. The differential amplifier is an amplifier configured to amplify a difference in an input differential voltage signal, and corresponds to, for example, an instrumentation amplifier (IA).

The output signal of the amplifier 240 is transmitted to the signal processor 250 and the controller 220.

The switching circuit 230 controls connections between input terminals of the amplifier 240 and paths along which the differential voltage signal obtained by the differential voltage signal receiver 210 is transmitted. The switching circuit 230 changes the connections based on a control signal output from the controller 220. The switching circuit 230 includes, for example, a chopper circuit configured to control connections between the input terminals of the amplifier 240 and paths along which the first and second voltage signals included in the differential voltage signal are supplied. The chopper circuit adjusts a polarity of the differential voltage signal input into the amplifier 240.

The chopper circuit reverses the connections based on the control signal output from the controller 220. For example, it is assumed that a first line along which the first voltage signal is transmitted is connected to a first input terminal of the amplifier 240, and a second line along which the second voltage signal is transmitted is connected to a second input terminal of the amplifier 240. If the connections are reversed by the chopper circuit, the first line is connected to the second input terminal, and the second line is connected to the first input terminal.

The reset circuit 260 inputs a reset signal into the input terminals of the amplifier 240 under the control of the controller 220. In response to the reset signal being input into the input terminals of the amplifier 240, the output signal of the amplifier 240 indicates a constant value. The reset circuit 260 may include a switching device that is controlled based on the control signal of the controller 220, and the switching device may be connected to input terminals of the amplifier 240, such that if the switching device is turned on, the input terminals of the amplifier 240 are connected to a fixed voltage end, for example, a predefined reference voltage Vref end.

The controller 220 controls an operation of the signal measurement apparatus 200 through the control signal. The controller 220 determines whether to output the control signal to control the switching circuit 230 based on a signal value of the output signal of the amplifier 240. In response to the signal value of the output signal of the amplifier 240 satisfying a predefined condition, the controller 220 outputs the control signal to control the switching circuit 230. The controller 220 generates a control signal that is toggled each time the output signal of the amplifier 240 reaches a preset threshold value.

For example, in response to the signal value of the output signal of the amplifier 240 reaching a first threshold value, the controller 220 outputs a control signal to change the connections of the switching circuit 230. The switching circuit 230 operates based on the control signal, such that the connections between the input terminals of the amplifier 240 and the paths along which the differential voltage signal is transmitted are reversed. In response to the signal value of the output signal of the amplifier 240 reaching the first threshold value and then reaching a second threshold value, the controller 220 outputs a control signal to change the connections of the switching circuit 230. In this example, the connections are changed to the original state. The first threshold value and the second threshold value are different values.

The controller 220 may include a counter (not shown) configured to count the number of times the signal value of the output signal of the amplifier 240 reaches a threshold value. The counter counts the number of times the signal value of the output signal of the amplifier 240 reaches at least one of the first threshold value and the second threshold value. The controller 220 resets a count value output from the counter in a time interval after the signal value of the output signal of the amplifier 240 is sampled. Here, the time interval is, for example, a time interval from a time corresponding to a 180-degree phase of the current source to a time corresponding to a 360-degree phase of the current source. For example, the signal value is sampled at a time corresponding to a 90-degree phase of the current source. Herein, the time corresponding to the 90-degree phase corresponds to a 1/4 cycle, and the time corresponding to the 180-degree phase corresponds to a 1/2 cycle. A time corresponding to a 270-degree phase corresponds to a 3/4 cycle, and the time corresponding to the 360-degree phase corresponds to a 4/4 cycle.

The controller 220 outputs a control signal to input a reset signal into the input terminals of the amplifier 240 during a time interval after the signal value of the output signal of the amplifier 240 is sampled. The time interval is, for example, a time interval from the time corresponding to the 180-degree phase of the current source to the time corresponding to the 360-degree phase of the current source. The controller 220 receives phase information of the current signal output from the current source, and generates the control signal to control the reset signal based on the received phase information. The reset circuit 260 operates based on the control signal, such that the reset signal, for example, a fixed voltage Vref, is input into the input terminals of the amplifier 240. In response to the reset signal being input into the input terminals of the amplifier 240, the output signal of the amplifier 240 indicates a constant value.

The signal processor 250 processes the output signal of the amplifier 240. For example, the signal processor 250 performs signal processing, such as sampling the signal value, for example, a peak value, in the output signal of the amplifier 240 and converting the sampled signal value to a digital signal. For example, the sampling is performed at each time corresponding to the 90-degree phase of the current source. An actual signal value of the output signal is estimated based on the signal value of the output signal of the amplifier 240 at the time corresponding to the 90-degree phase of the current source, the count value determined by the counter, and the threshold value. An example of estimating an actual signal value will be described below with reference to FIG. 5.

Figure 3A:
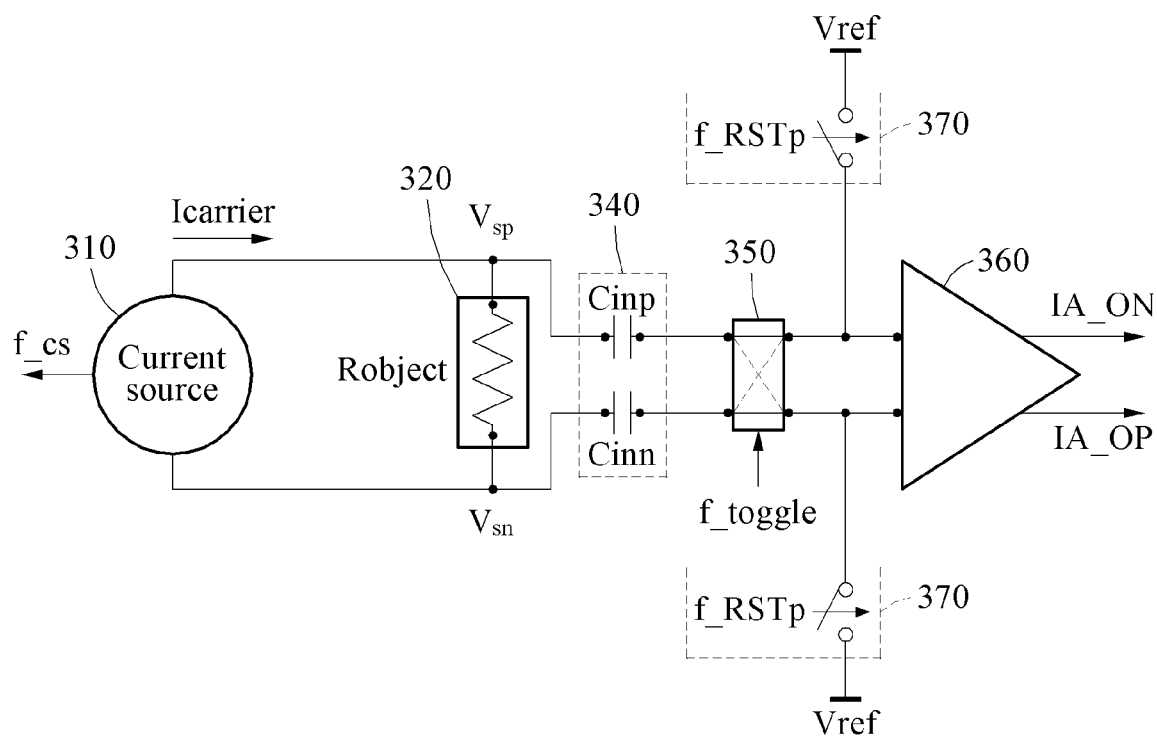
FIGS. 3A and 3B are circuit diagrams illustrating an example of implementing a signal measurement apparatus, in accordance with one or more embodiments.
Figure 3B:
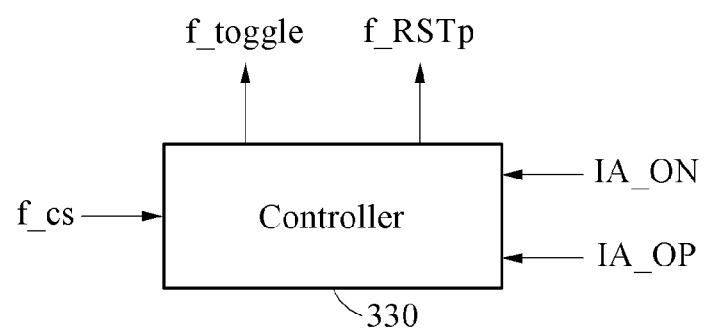

FIGS. 3A and 3B are circuit diagrams illustrating an example of implementing a signal measurement apparatus, in accordance with one or more embodiments.

Referring to FIGS. 3A and 3B, a current source 310 supplies a current signal Icarrier with a carrier frequency f_cs to a measurement object 320. Information related to the current signal Icarrier may be known. For example, information related to a waveform, a magnitude, and a frequency of the current signal Icarrier may be predefined. In response to the current signal Icarrier being supplied to the measurement object 320, voltage signals $V_{sp}$ and $V_{sn}$ are induced by an impedance component Robject of the measurement object 320. A signal measurement apparatus senses the induced voltage signals $V_{sp}$ and $V_{sn}$ in the form of a differential voltage signal. In the circuit of FIG. 3A, a terminal at which the current signal Icarrier is supplied to the measurement object 320 and a terminal at which the voltage signals $V_{sp}$ and $V_{sn}$ are measured, are illustrated to be bound as a common node. In reality, the terminal at which the current signal Icarrier is supplied and the terminal at which the voltage signals $V_{sp}$ and $V_{sn}$ are measured, are nodes which are arranged on the object 320 and may be different from each other. Further, if there is a plurality of current sources, a plurality of terminals at which current signals are supplied from the corresponding current sources may be positioned at different parts of the measurement object 320. Further, if there is a plurality of measurement channels for measuring voltage signals induced by the current signals, a plurality of terminals for measuring the voltage signals may be positioned at different parts of the measurement object 320.

The differential voltage signal sensed from the measurement object 320 is transmitted to capacitors Cinp and Cinn 340. The capacitors Cinp and Cinn 340 remove a direct voltage component from the sensed differential voltage signal and output the result differential voltage signal to a switching circuit 350. The switching circuit 350 transmits signals of alternating voltage components in the sensed differential voltage signal.

The switching circuit 350 controls connections between input terminals of an amplifier 360 and paths along which the differential voltage signal is transmitted, based on a control signal f_toggle output from a controller 330 (FIG. 3B). The switching circuit 350 includes a chopper circuit configured to control the connections. One side of the chopper circuit is connected to the capacitors Cinp and Cinn 340, and the other side thereof is connected to the input terminals of the amplifier 360 and one end of a reset circuit 370.

If the control signal f_toggle changes from a high logic state to a low logic state or conversely changes from a low logic state to a high logic state, the chopper circuit reverses the connections.

For example, it is assumed that a first line along which the first voltage signal of the differential voltage signal is transmitted from the first capacitor Cinp is connected to the first input terminal of the amplifier 360, and a second line along which the second voltage signal of the differential voltage signal is transmitted from the second capacitor Cinn is connected to the second input terminal of the amplifier 360. The chopper circuit maintains previous connections until the logic state of the control signal f_toggle changes, and reverses the connections if the logic state of the control signal f_toggle changes to the other logic state. In this example, the first line is connected to the second input terminal of the amplifier 360, and the second line is connected to the first input terminal of the amplifier 360.

The amplifier 360 amplifies the differential voltage signal received from the capacitors Cinp and Cinn 340 through the switching circuit 350, and outputs the amplified differential voltage signal. The output signals IA_ON and IA_OP of the amplifier 360 are transmitted to the controller 330 (FIG. 3B) and a signal processor (not shown) for signal processing. In an example, the amplifier 360 may operate in a single-ended mode to receive a single voltage signal and generate a single output signal or to receive the differential voltage signal and generate a single output signal. In an example of the amplifier 360 receiving a single voltage signal, the single voltage signal is input into one input terminal of the amplifier 360, and a reference voltage, for example, Vref, with a predetermined voltage value or a common mode signal of the single voltage signal is supplied to the other input terminal.

The reset circuit 370 resets an input of the input terminals of the amplifier 360 based on a control signal f_RSTp output from the controller 330. The reset circuit 370 includes a switching device configured to input the reset signal, for example, Vref, into the input terminals of the amplifier 360. One end of the switching device is connected to a supply end which supplies the reset signal, and the other end of the switching device is connected to one input terminal of the amplifier 360. The switching device is turned off if a logic state of the control signal f_RSTp is a low logic state, and is turned on if the logic state of the control signal f_RSTp is a high logic state. In response to the switching device being turned on, the reset signal is input into the input terminals of the amplifier 360.

The controller 330 controls the operations of the components of the signal measurement apparatus through control signals. For example, the controller 330 generates the control signal f_toggle to control the switching circuit 350 and the control signal f_RSTp to control the reset circuit 370. The controller 330 receives information related to the carrier frequency f_cs of the current signal Icarrier from the current source 310, and receives the output signals IA_ON and IA_OP from the amplifier 360.

The controller 330 compares one of the output signals IA_ON and IA_OP of the amplifier 360 to a threshold value, and outputs the control signal f_toggle to change the connections of the switching circuit 350 in response to the output signal reaching the threshold value. Thereafter, in response to the output signal of the amplifier 360 reaching another threshold value, the controller 330 outputs the control signal f_toggle to change the connections of the switching circuit 350. The controller 330 counts the number of times the output signal reaches the threshold values within one cycle from a 0-degree phase to a 360-degree phase.

The controller 330 outputs a control signal f_RSTp to turn on the switching device included in the reset circuit 370 after a predetermined phase. For example, the controller 330 turns off the switching device during a time interval from a 0-degree phase to a 180-degree phase, and turns on the switching device during a time interval from a time corresponding to the 180-degree phase to a time corresponding to a 360-degree phase of the corresponding current source.

Figure 4:
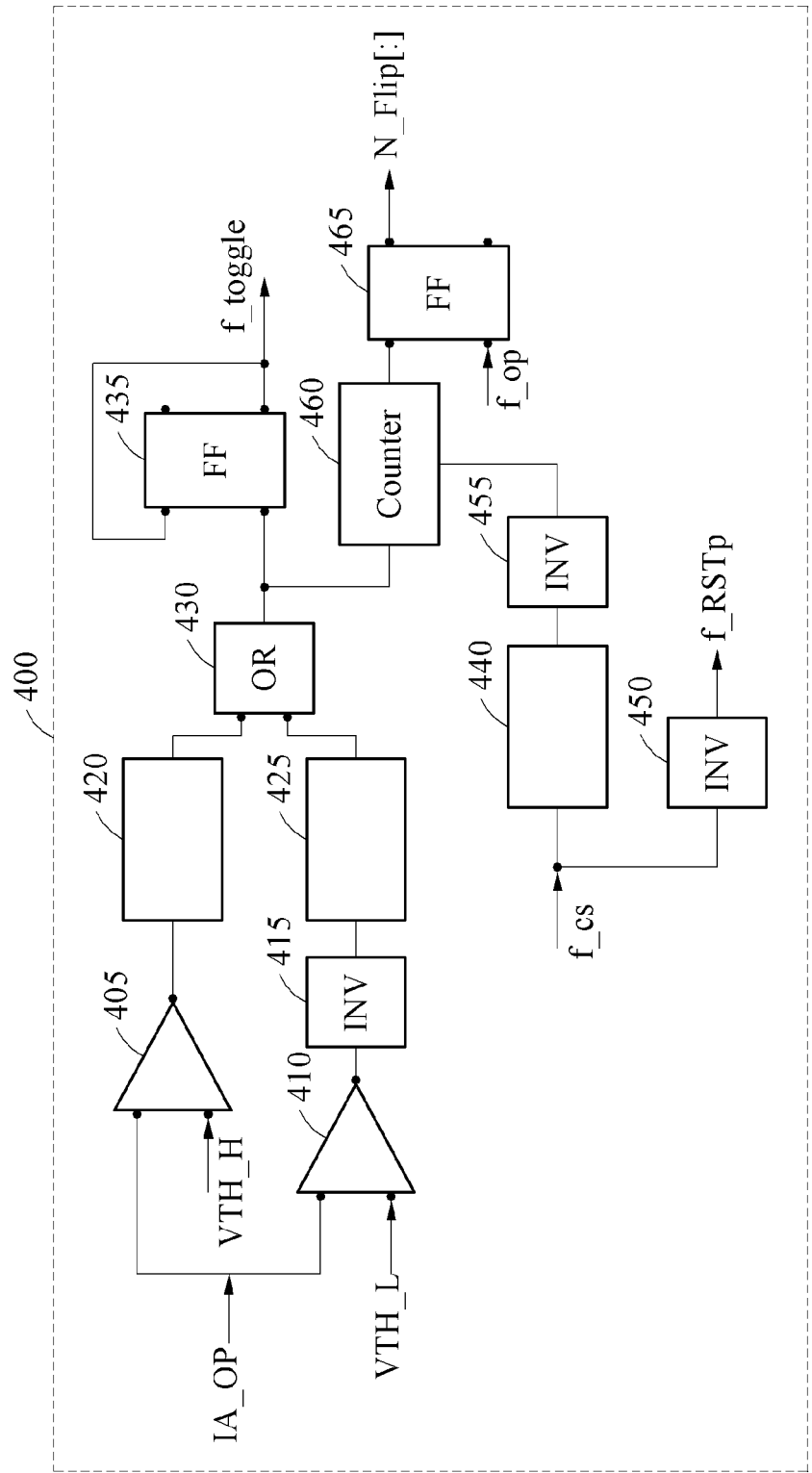
FIG. 4 illustrates an example of a configuration of a controller, in accordance with one or more embodiments.

FIG. 4 illustrates an example of a configuration of a controller, in accordance with one or more embodiments.

Referring to FIG. 4, a controller 400 is implemented as logic gates. In the example of FIG. 4, it is assumed that the controller 400 performs a control process based on one of output signals IA_ON and IA_OP, in detail, the output signal IA_OP, of an amplifier. First, the output signal IA_OP is transmitted to a first comparator 405 and a second comparator 410. The first comparator 405 compares the output signal IA_OP to a first threshold value VTH_H, and outputs a value of a high logic state in response to a signal value of the output signal IA_OP being greater than the first threshold value VTH_H. The output value of the first comparator 405 is transmitted to a first pulse signal generator 420, and the first pulse signal generator 420 generates and outputs a pulse signal at a rising edge of the output value.

The second comparator 410 compares the output signal IA_OP to a second threshold value VTH_L, and outputs a value of a high logic state in response to the signal value of the output signal IA_OP being greater than the second threshold value VTH_L. The value output from the second comparator 410 is inverted by a first inverter 415. An output value of the first inverter 425 is transmitted to a second pulse signal generator 425, and the second pulse signal generator 425 generates and outputs a pulse signal at a rising edge of the output value.

The output values of the first pulse signal generator 420 and the second pulse signal generator 425 are transmitted to an OR logic gate 430, and a result value calculated by the OR logic gate 430 is transmitted to a first flip flop 435 and a counter 460. The counter 460 generates a result value obtained by counting the number of times the output signal IA_OP reaches the first threshold value VTH_H or the second threshold value VTH_L, and transmits the generated result value to a second flip flop 465. The second flip flop 465 outputs a final count value N_Flip[:] corresponding to the number of times the output signal IA_OP reaches the first threshold value VTH_H or the second threshold value VTH_L, based on a predetermined clock signal f_op. The second flip flop 465 updates the output value of the counter 460 to the count value N_Flip[:] for each rising edge of the predetermined clock signal f_op, and maintains the updated count value.

The carrier frequency f_cs of the current signal supplied from the current source is transmitted to a third pulse signal generator 440 and a second inverter 450. A control signal f_RSTp to control a reset circuit is output from the second inverter 450. The third pulse signal generator 440 generates and outputs a pulse signal at a rising edge of the carrier frequency f_cs, and the output pulse signal is transmitted to a third inverter 455. A pulse signal inverted by the third inverter 455 is transmitted to the counter 460.

Figure 5:
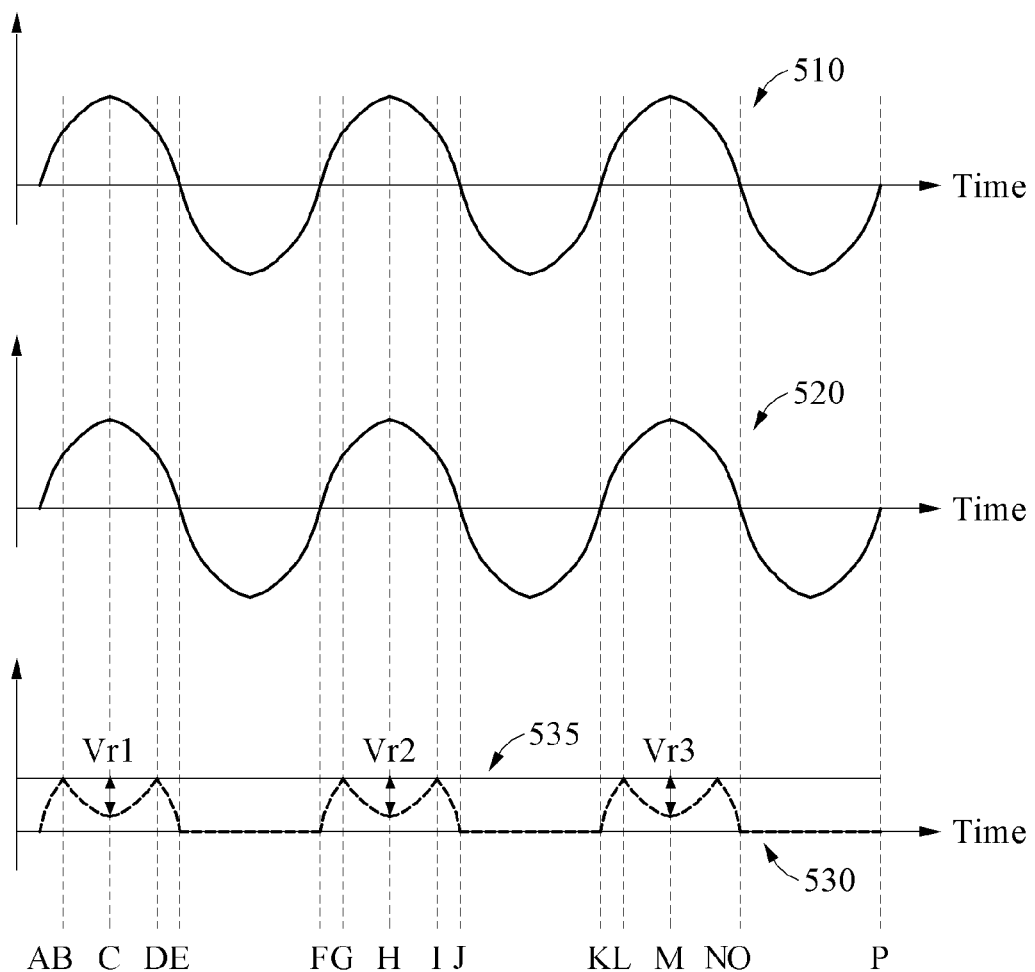
FIGS. 5 and 6 illustrate examples of signal waveforms to describe an operation of a signal measurement apparatus, in accordance with one or more embodiments.

FIG. 5 illustrates an example of signal waveforms to describe an operation of a signal measurement apparatus, in accordance with one or more embodiments.

Referring to FIG. 5, a signal waveform 510 is a signal waveform of a current signal output from a current source, and a signal waveform 520 is a signal waveform of a voltage signal induced by supplying the output current signal of the current source to a measurement object. The signal waveform of the current signal is, for example, a sine wave. However, examples are not limited thereto. A signal waveform 530 is a signal waveform of an output signal of an amplifier.

For example, the signal waveform 510 corresponds to the current signal Icarrier described in FIG. 3, and the signal waveform 520 corresponds to the voltage signal $V_{sp}$ passing through the capacitor Cinp. The signal waveform 530 corresponds to the output signal IA_OP of the amplifier 360. In the graphs showing the signal waveforms 510, 520, and 530, the horizontal axis indicates a flow of time, and the vertical axis indicates a magnitude of a signal. The signal waveforms 510, 520, and 530 are synchronized in terms of time, but have different scales of signal magnitude. In the signal waveforms 510, 520, and 530, A, F, and K are times corresponding to a 0-degree phase, and C, H, and M are times corresponding to a 90-degree phase. E, J, and O are times corresponding to a 180-degree phase, and F, K, and P are times corresponding to a 360-phase which is the same as the 0-degree phase. A time interval from the time A to the time F, a time interval from the time F to the time K, and a time interval from the time K to the time P each correspond to one cycle.

Referring again to FIGS. 3A and 3B, in conjunction with FIG. 5, the controller 330 monitors the output signal IA_OP of the amplifier 360, and outputs a control signal f_toggle to change the connections of the switching circuit 350 at the time B at which the signal value of the output signal IA_OP reaches a threshold value 535 corresponding to an upper limit. In this example, the differential voltage signal with reversed polarities is input into the amplifier 360 through the switching circuit 350, and the voltage signal $V_{sn}$ passing through the capacitor Cinn is reflected in the output signal IA_OP from the time B. Thus, the output signal IA_OP starts falling from the time B. Although not expressed in the signal waveform 530, in response to the falling signal reaching a threshold value corresponding to a lower limit, the controller 330 outputs the control signal f_toggle again to change the connections of the switching circuit 350.

The output signal IA_OP of the amplifier 360 reaches the threshold value 535 again at the time D, and the connections of the switching circuit 350 are changed based on by the control signal f_toggle at the time D. The controller 330 counts, through the counter, the number of times the output signal of the amplifier 360 reaches the threshold value 535 corresponding to the upper limit and the threshold value corresponding to the lower limit.

A signal measurement apparatus samples the signal value of the output signal IA_OP at each of the times C, H, and M corresponding to the 90-degree phase, and performs analog-to-digital conversion. The signal measurement apparatus restores an actual signal value based on the count value counted by the controller 330 and difference values Vr1, Vr2, and Vr3 between the threshold value 535 and the sampled signal values. For example, an actual signal value of the output signal IA_OP at the time C corresponds to a result value obtained by adding the threshold value 535 and the difference value Vr1. If the resistance of a measurement object changes over time, a measured signal value also changes. Thus, the difference values Vr1, Vr2, and Vr3 between the threshold value 535 and the signal values at the times corresponding to the 90-degree phase are also proportional to the measured signal values. The analog-to-digital conversion processing is performed based on the signal values measured at the times C, H, and M.

The controller 330 resets the count value of the counter and the input of the amplifier 360 in a predetermined phase interval. The controller 330 sets a cyclical reference point by resetting the input of the amplifier 360. For example, each of the times corresponding to the 0-degree phase is set as the reference point through the resetting process. The controller 330 controls the reset circuit 370 to supply a fixed voltage signal to the input terminals of the amplifier 360 during a time interval from the time E corresponding to the 180-degree phase to the time F corresponding to the 360-degree phase. A start time of reset may be any time which secures a sufficient time for reset. A time corresponding to any phase in each cycle may be selected as an end time of reset.

Figure 6:
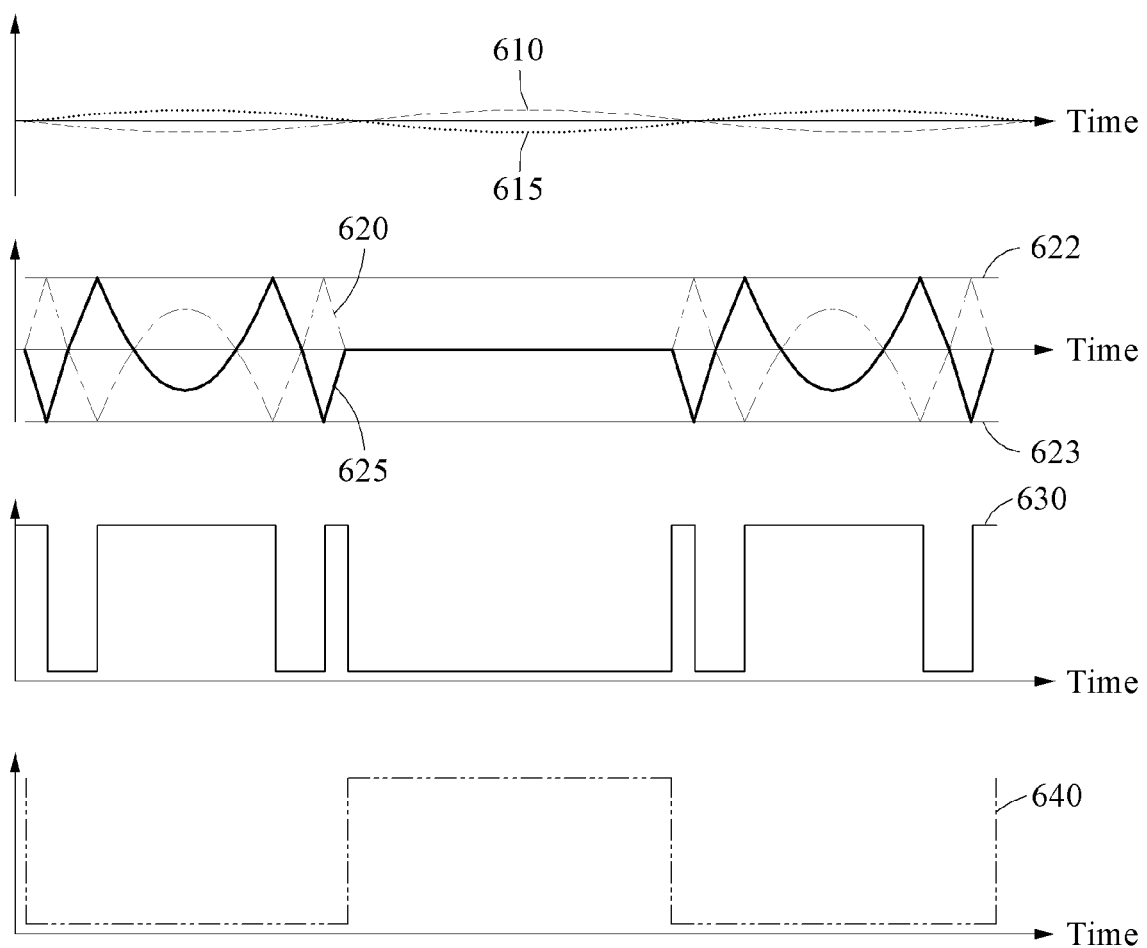

FIG. 6 illustrates an example of signal waveforms to describe an operation of a signal measurement apparatus, in accordance with one or more embodiments.

Referring to FIG. 6, signal waveforms 610 and 615 are signal waveforms of the differential voltage signal input into the amplifier 360, and signal waveforms 620 and 625 are signal waveforms of the differential output signal of the amplifier 360. In the signal waveforms 620 and 625, a first threshold value 622 corresponding to an upper limit and a second threshold value 623 corresponding to a lower limit are indicated. A signal waveform 630 is a signal waveform of the control signal f_toggle supplied to the switching circuit 350, and a signal waveform 640 is a signal waveform of the control signal f_RSTp supplied to the reset circuit 370.

In the graphs showing the signal waveforms 610, 615, 620, 625, 630, and 640, the horizontal axis indicates a flow of time, and the vertical axis indicates a magnitude of a signal. The signal waveforms 610, 615, 620, 625, 630, and 640 are synchronized in terms of time, but have different scales of signal magnitude.

Referring to the signal waveforms 620 and 625 of the differential output signal of the amplifier 360, it is evident that the signal value of the output signal of the amplifier 360 reaches the first threshold value 622 and then reaches the second threshold value 623 again within the time interval from the time of the 0-degree phase to the time of the 90-degree phase, such that the connections of the switching circuit 350 are changed two times. Referring to the signal waveform 630 of the control signal f_toggle, the logic states are reversed each time the differential output signal of the amplifier 360 reaches the first threshold value or the second threshold value. Referring to the signal waveform 640 of the control signal f_RSTp, it is evident that the control signal f_RSTp is maintained to be in a high logic state during a predetermined phase interval, for example, an interval from the 180-degree phase to the 360-degree phase, such that the reset circuit 370 resets the input value of the amplifier 360.

FIG. 7 illustrates an example of a signal measurement method, in accordance with one or more embodiments. The operations in FIG. 7 may be performed in the sequence and manner as shown, although the order of some operations may be changed or some of the operations omitted without departing from the spirit and scope of the illustrative examples described. Many of the operations shown in FIG. 7 may be performed in parallel or concurrently. One or more blocks of FIG. 7, and combinations of the blocks, can be implemented by special purpose hardware-based computer that perform the specified functions, or combinations of special purpose hardware and computer instructions. A signal measurement method is performed by a signal measurement apparatus described herein.

Referring to FIG. 7, in operation 710, the signal measurement apparatus supplies a current signal to a measurement object. The signal measurement apparatus supplies an alternating current signal with a predetermined carrier frequency to the measurement object through a current source.

In operation 720, the signal measurement apparatus obtains a differential voltage signal induced by the current signal from the measurement object. The differential voltage signal induced by the current signal includes an impedance characteristic of the measurement object.

In operation 725, the signal measurement apparatus determines whether a signal value of an output signal of an amplifier into which the differential voltage signal is input satisfies a condition. For example, the signal measurement apparatus determines whether the signal value of the output signal reaches a predefined threshold value.

In response to the signal value of the output signal of the amplifier satisfying the condition, the signal measurement apparatus changes connections between input terminals of the amplifier and paths along which the differential voltage signal is transmitted, in operation 730. The signal measurement apparatus changes the connections using a switching circuit positioned between the paths along which the differential voltage signal is transmitted and the amplifier. For example, in response to the signal value of the output signal of the amplifier reaching a first threshold value, the signal measurement apparatus changes the connections, such that the connections are reversed. In response to the signal value of the output signal of the amplifier reaching the first threshold value and then reaching a second threshold value, the signal measurement apparatus changes the connections to an original state. Here, the first threshold value and the second threshold value respectively correspond to an upper limit and a lower limit, or a lower limit and an upper limit.

In operation 740, the signal measurement apparatus resets an input value of the amplifier during a time interval after the signal value of the output signal of the amplifier is sampled. The time interval may be, for example, a time interval from a time corresponding to a 180-degree phase of a current source to a time corresponding to a 360-degree phase of the current source. The signal measurement apparatus inputs a reset signal, for example, a fixed voltage signal, into the input terminals of the amplifier, using a reset circuit including a switching device, during the time interval.

The signal measurement apparatus determines a count value by counting the number of times the signal value of the output signal of the amplifier reaches a threshold value, and estimates an actual signal value of the output signal based on the determined count value and the signal value sampled from the output signal of the amplifier. The signal measurement apparatus estimates the actual signal value of the output signal based on a signal value of the output signal of the amplifier at a time corresponding to a 90-degree phase of the current source, the determined count value, and the threshold value.

The description provided with reference to FIGS. 1 through 6 also applies to an operation of the signal measurement apparatus not described in FIG. 7, and thus duplicated description will be omitted for conciseness.

The signal measurement apparatuses 110 and 200, the current source 120, the signal processing circuit 130, the differential voltage signal receiver 210, the capacitor 215, the switching circuit 230, the amplifier 240, the signal processor 250, the reset circuit 260, the controller 220, the controller 330, the controller 400 described herein with respect to FIGS. 1-7 are implemented as and by hardware components. Examples of hardware components that may be used to perform the operations described in this application where appropriate include controllers, sensors, generators, drivers, memories, comparators, arithmetic logic units, adders, subtractors, multipliers, dividers, integrators, and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 1-7 that perform the operations described in this application are performed by computing hardware, for example, by one or more processors or computers, implemented as described above executing instructions or software to perform the operations described in this application that are performed by the methods. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller. One or more processors, or a processor and a controller, may perform a single operation, or two or more operations.

Instructions or software to control a processor or computer to implement the hardware components and perform the methods as described above are written as computer programs, code segments, instructions or any combination thereof, for individually or collectively instructing or configuring the processor or computer to operate as a machine or special-purpose computer to perform the operations performed by the hardware components and the methods as described above. In one example, the instructions or software include machine code that is directly executed by the processor or computer, such as machine code produced by a compiler. In another example, the instructions or software include higher-level code that is executed by the processor or computer using an interpreter. The instructions or software may be written using any programming language based on the block diagrams and the flow charts illustrated in the drawings and the corresponding descriptions in the specification, which disclose algorithms for performing the operations performed by the hardware components and the methods as described above.

The instructions or software to control computing hardware, for example, one or more processors or computers to implement the hardware components and perform the methods as described above, and any associated data, data files, and data structures, may be recorded, stored, or fixed in or on one or more non-transitory computer-readable storage media. Examples of a non-transitory computer-readable storage medium include read-only memory (ROM), random-access programmable read only memory (PROM), electrically erasable programmable read-only memory (EEPROM), random-access memory (RAM), dynamic random access memory (DRAM), static random access memory (SRAM), flash memory, non-volatile memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, blue-ray or optical disk storage, hard disk drive (HDD), solid state drive (SSD), flash memory, a card type memory such as multimedia card micro or a card (for example, secure digital (SD) or extreme digital (XD)), magnetic tapes, floppy disks, magneto-optical data storage devices, optical data storage devices, hard disks, solid-state disks, and any other device that is configured to store the instructions or software and any associated data, data files, and data structures in a non-transitory manner and provide the instructions or software and any associated data, data files, and data structures to one or more processors or computers so that the one or more processors or computers can execute the instructions. In one example, the instructions or software and any associated data, data files, and data structures are distributed over network-coupled computer systems so that the instructions and software and any associated data, data files, and data structures are stored, accessed, and executed in a distributed fashion by the one or more processors or computers.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A signal measurement apparatus comprising:
an amplifier configured to:
receive a differential voltage signal;
amplify the received differential voltage signal; and
output the amplified differential voltage signal; and
a controller configured to output, in response to a signal value of the amplified differential voltage signal satisfying a condition, a control signal to control a switching circuit configured to transmit the differential voltage signal to the amplifier, the switching circuit includes a first connection connecting to a first input terminal of the amplifier, and a second connection connecting to a second input terminal of the amplifier;
wherein the switching circuit is configured to, based on the control signal, reverse the first and second connections between the first and the second input terminals, and
wherein the controller is further configured to output a control signal to change a connection of the switching circuit, in response to the signal value of the amplified differential voltage signal reaching a first threshold value.

2. The signal measurement apparatus of claim 1, wherein the reversing of the first and second connections is by connecting the first connection to the second input terminal and connecting the second connection to the first input terminal.

3. The signal measurement apparatus of claim 1, wherein the controller is further configured to output the control signal to change the connection of the switching circuit, in response to the signal value of the output signal of the amplifier reaching the first threshold value and then reaching a second threshold value,
wherein the first threshold value and the second threshold value are different values.

4. The signal measurement apparatus of claim 1, wherein the controller comprises:
a counter configured to count a number of times the signal value of the amplified differential voltage signal reaches a threshold value.

5. The signal measurement apparatus of claim 4, wherein the controller is further configured to reset a count value output from the counter in a time interval after the signal value of the amplified differential voltage signal is sampled.

6. The signal measurement apparatus of claim 4, wherein an actual signal value of the amplified differential voltage signal is estimated based on the signal value of the amplified differential voltage signal at a time corresponding to a 90-degree phase of a current source, a determined count value of the counter, and the threshold value.

7. The signal measurement apparatus of claim 1, wherein the controller is further configured to output a control signal to input a reset signal into the input terminals of the amplifier during a time interval after the signal value of the amplified differential voltage signal is sampled.

8. The signal measurement apparatus of claim 7, wherein in response to the reset signal being input to the input terminals of the amplifier, the amplified differential voltage signal indicates a constant value.

9. The signal measurement apparatus of claim 7, wherein the time interval is a time interval from a time corresponding to a 180-degree phase of the current source to a time corresponding to a 360-degree phase of the current source.

10. The signal measurement apparatus of claim 1, wherein the switching circuit includes a chopper circuit configured to control connections between the input terminals of the amplifier and paths along which first and second voltage signals included in the differential voltage signal are supplied.

11. A signal measurement method comprising:
transmitting, by a signal measurement apparatus, a current signal to a measurement object;
receiving, by the signal measurement apparatus, a differential voltage signal induced by the current signal from the measurement object;
inputting the received differential voltage signal to an amplifier; and
in response to a signal value of an output signal of the amplifier satisfying a condition, reversing connections between input terminals of the amplifier and paths along which the differential voltage signal is transmitted in which the connections include a first connection connecting to a first input terminal of the amplifier and a second connection connecting to a second input terminal of the amplifier,
wherein the reversing of the connections comprises reversing the connections in response to the signal value of the output signal of the amplifier reaching a first threshold value.

12. The signal measurement method of claim 11, wherein the reversing of the connections comprises reversing the first and second connections with a switching circuit positioned between the paths and, based on the control signal, reverse the first and second connections by connecting the first connection to the second input terminal and connecting the second connection to the first input terminal.

13. The signal measurement method of claim 11, wherein the changing of the connections further comprises changing the connections to an original state in response to the signal value of the output signal of the amplifier reaching the first threshold value and then reaching a second threshold value.

14. The signal measurement method of claim 11, wherein the signal measurement apparatus is configured to:
count a number of times the signal value of the output signal of the amplifier reaches a threshold value, and
estimate an actual signal value of the output signal of the amplifier based on a signal value of the output signal of the amplifier at a time corresponding to a 90-degree phase of a current source, a determined count value, and the threshold value.

15. The signal measurement method of claim 11, further comprising:
resetting an input value of the amplifier during a time interval after the signal value of the output signal of the amplifier is sampled.

16. A non-transitory computer-readable storage medium storing instructions that, when executed by a processor, cause the processor to perform the signal measurement method of claim 11.

17. A signal measurement apparatus comprising:
a receiver configured to receive a measured differential voltage signal;
a capacitor configured to remove a voltage component from the differential voltage signal and output a resultant differential voltage signal;
a switching circuit configured to receive the resultant differential voltage signal and adjust a polarity of the resultant differential voltage signal by reversing connections between input terminals of the amplifier and paths along which first and second voltage signal included in the received differential voltage signal are supplied; and
an amplifier configured to receive the adjusted resultant differential voltage signal, amplify the adjusted resultant differential voltage signal, and output the amplified signal,
wherein the switching circuit is further configured to reverse the connections in response to a signal value of the amplified signal reaching a first threshold value.

18. The signal measurement apparatus of claim 17, wherein the switching circuit includes a chopper circuit configured to control the connections between the input terminals of the amplifier and the paths.

* * * * *